United States Patent [19]

Kanda et al.

[11] Patent Number: 5,054,915

[45] Date of Patent: * Oct. 8, 1991

[54] LIVER FUNCTION TESTING APPARATUS

[75] Inventors: Masahiko Kanda; Kunio Awazu, both of Osaka, Japan

[73] Assignee: Sumitomo Electric Industries, Ltd., Osaka, Japan

[ * ] Notice: The portion of the term of this patent subsequent to Mar. 6, 2007 has been disclaimed.

[21] Appl. No.: 270,223

[22] Filed: Nov. 14, 1988

[30] Foreign Application Priority Data

Nov. 13, 1987 [JP] Japan .................................. 62-287677
Nov. 13, 1987 [JP] Japan .................................. 62-287679

[51] Int. Cl.⁵ ............................................. G01N 33/48
[52] U.S. Cl. ........................................ 356/39; 356/41; 128/666
[58] Field of Search .................................... 356/39–42, 356/51, 72, 410, 418, 320; 250/218, 328; 128/665–667, 633

[56] References Cited

U.S. PATENT DOCUMENTS 4,100,416  7/1978  Hirschfeld ........................... 356/307
4,266,554  5/1981  Hamaguri ............................. 356/41
4,905,703  3/1990  Kanda et al. ......................... 128/666

Primary Examiner—Davis L. Willis
Assistant Examiner—Hoa Pham
Attorney, Agent, or Firm—W. G. Fasse; D. H. Kane, Jr.

[57] ABSTRACT

A liver function testing apparatus, provides light signals (11, 12) exposing vital tissue (15) to a first light signal that is substantially absorbed by a specific dye dosed into the blood of the vital tissue. The dye is to be taken in and removed by the liver. A second light signal is substantially not absorbed by the specific dye. Optical pulses obtained from the vital tissue are received by a light receiving element (13), the output of which is sampled by an A-D converter (30) to provide digital output signals. On the basis of variable components in the blood, a CPU (34) determines a coefficient of a regression line expression between first and second photoelectric conversion signals, to perform a biocalibration. A value correlated with a specific dye concentration in the blood, is processed on the basis of sampling signals during a prescribed period after an injection of the specific dye and the determined coefficient of the regression line expression, so that a coefficient of a simulation function is obtained as a function of time using the method of least squares. Additionally, an index RMAX expressing the total amount of hepatic cell function is obtained on the basis of the coefficients.

15 Claims, 17 Drawing Sheets

FIG.1

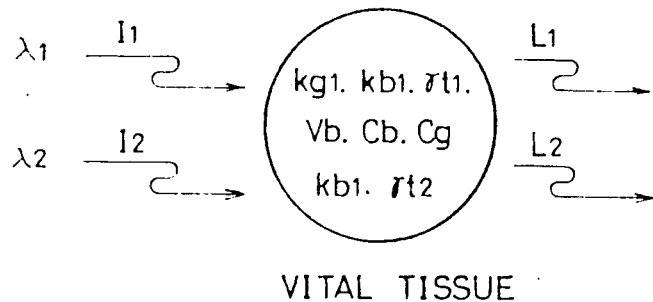

VITAL TISSUE

- kg1 : ABSORPTION COEFFICIENT OF SPECIFIC DYE (WAVELENGTH $\lambda_1$)
- kg2 : ABSORPTION COEFFICIENT OF BLOOD AT WAVELENGTH $\lambda_1$
- kb2 : ABSORPTION COEFFICIENT OF BLOOD AT WAVELENGTH $\lambda_2$
- $\gamma t_1$ : ABSORBANCE OF TISSUE AT WAVELENGTH $\lambda_1$
- $\gamma t_2$ : ABSORBANCE OF TISSUE AT WAVELENGTH $\lambda_2$
- Vb : BLOOD VOLUME IN SAMPLE
- Cb : BLOOD CONCENTRATION IN SAMPLE
- Cg : SPECIFIC DYE CONCENTRATION IN SAMPLE

FIG.2

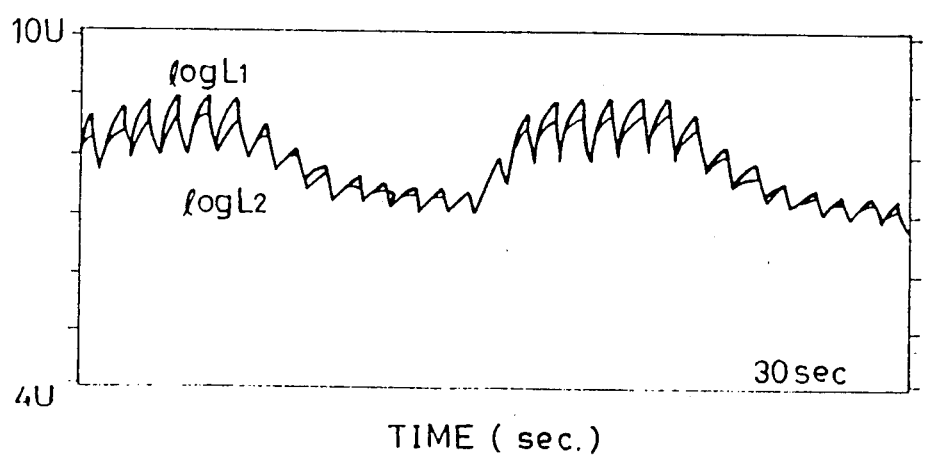

TIME (sec.)

| | |
|---|---|
| L1 | —8a1 |
| L2 | —8a1 |
| LMAX | —8b1 |
| LMIN | —8b2 |
| m | |
| i1 | —8c1 |
| I2 | —8c2 |
| CL1(1) | —8d1 |
| ⌇ | ⌇ |
| CL1(n) | —8dn |
| ITM | —8i1 |
| TIM1 | —8i2 |
| TIM2 | —8i3 |
| k1 | —8k1 |
| rg1 | —8k2 |
| k2 | —8k3 |
| rg2 | —8k4 |
| k3 | —8k5 |
| rg3 | —8k6 |
| CL2(1) | —8e1 |
| ⌇ | ⌇ |
| CL2(n) | —8en |
| A | —8f1 |
| B | —8f2 |
| r1 | —8f3 |
| CL10 | —8f4 |
| Cg(1) | —8g1 |
| ⌇ | ⌇ |
| Cg(m) | —8gm |
| LOλ1 | —8h1 |
| LOλ2 | —8h2 |
| RMAX | —8ℓ1 |
| rMAX | —8ℓ2 |
| D1 | —8j |

| | |
|---|---|
| L1 | 8a1 |
| L2 | 8a2 |
| LMAX | 8b1 |
| LMIN | 8b2 |
| m | |
| i1 | 8c1 |
| i2 | 8c2 |
| CL1(1) | 8d1 |
| ⌇ | ⌇ |
| CL1(n) | 8dn |
| ITM | 8i1 |
| TIM1 | 8i2 |
| TIM2 | 8i3 |
| k1 | 8k1 |
| rg1 | 8k2 |
| k2 | 8k3 |
| rg2 | 8k4 |
| k3 | 8k5 |
| rg3 | 8k6 |
| CL2(1) | 8e1 |
| ⌇ | ⌇ |
| CL2(n) | 8en |
| A | 8f1 |
| B | 8f2 |
| r1 | 8f3 |
| CL1o | 8f4 |
| Cg(1) | 8g1 |
| ⌇ | ⌇ |
| Cg(m) | 8gm |
| LOλ1 | 8h1 |
| LOλ2 | 8h2 |
| D | 8j1 |
| K | 8j2 |
| R | 8j3 |
| r2 | 8j4 |

LIVER FUNCTION TESTING APPARATUS

FIELD OF THE INVENTION

The present invention relates to a liver function testing apparatus, and more specifically, it relates to a liver function testing apparatus for automatically performing measurement for testing or diagnosing the function of a liver by injecting a specific color dye into the patient's blood stream, which is selectively taken in and removed by the liver. An index RMAX expressing the total amount of hepatic cell function is also measured.

BACKGROUND INFORMATION

An index RMAX expressing the total amount of hepatic cell function is precisely evaluated and used for judging an adaptation to an operation in the domain of liver surgery. The index also helps in comprehending a case of a hepatic disease and to judge any convalescence in the domain of medicine.

In a conventional method of measuring the index RMAX, blood for a blank test is first collected from a testee or patient. Then indocyanine green (hereinafter referred to as ICG) of 0.5 mg/kg is injected into the one antecubital vein within 30 seconds. Then blood samples of 3 to 4 ml are collected from the other antecubital vein after lapses of five, ten and fifteen minutes from starting the injection of the ICG solution. Then, 1 ml of the obtained blood is diluted in a physiological salt solution of 2 ml, and colorimetry is performed through a spectrophotometer with a blank of blood serum for the blank test at a wavelength of 805 nm. Reading (OD) in such colorimetry is plotted on semilogarithmic paper, whereby the ICG concentration from five to fifteen minutes is linearly decreased. Zero-order dye concentration in the blood is obtained from an intersection of a straight line connecting three points and the Y-axis. If a half value period ($t_{\frac{1}{2}}$) of a specific dye concentration in the blood is thereby obtained, a blood plasma disappearance rate K can be calculated from the following expression:

$$K = 0.693/t_{\frac{1}{2}} \text{ (liter/min)}$$

In the aforementioned three-point analysis method, the ICG injection must be performed three times while changing dose quantities. In that case, doses of ICG are considered in various ways. For example, a testee may be dosed with 0.5 mg/kg (patient's weight), 1.0 mg/kg and 5.0 mg/kg of ICG on different days, or measurement may be made with doses of 0.5 mg/kg, 1.0 mg/kg and 2.0 mg/kg. Or, ICG may be injected three times with doses of 0.5 mg/kg, 3.0 mg/kg and 5.0 mg/kg or twice with doses of 0.5 mg/kg and 5.0 mg/kg on different days. Further, the index RMAX may be measured in one day with doses of 0.5 mg/kg, 1.0 mg/kg and 5.0 mg/kg, or ICG may be injected three times on different days with doses of 0.5 mg/kg, 1.0 mg/kg and 2.0 mg/kg.

Blood collection and measurements of ICG concentration are performed similarly to the case of a dose of 0.5 mg/kg, to calculate the blood plasma disappearance rate K. The blood serum is initially diluted six to ten times, since the ICG concentration in blood is extremely high.

A method of calculating the index RMAX will now described.

Values of the blood plasma disappearance rate K with dose quantities of 0.5 mg/kg, 3.0 mg/kg and 5.0 mg/kg, for example, are 0.0568, 0.0376 and 0.0334 respectively. A liver removal ratio R is calculated from K (min.) × D (mg/kg), and hence:

$R = 0.0568 \times 0.5 = 0.0284$ when the dose quantity is 0.5 mg/kg, $R = 0.0376 \times 3.0 = 0.1128$ when the dose quantity is 3.0 mg/kg, and $R = 0.0334 \times 5.0 = 0.1671$ when the dose quantity is 5.0 mg/kg.

Then, the values are plotted as shown in FIG. 21, with the X-axis representing the inverse numbers $(1/D:(mg/kg)^{-1})$ of the dose quantities and the Y-axis representing the inverse numbers $(1/R:(mg/kg/min)^{-1})$ of the removal ratios.

The dose of 0.5 mg/kg is plotted as 2.00 on the X-axis and 35.21 on the Y-axis and the doses of 3.0 mg/kg is plotted as 0.33 on the X-axis and 8.86 on the Y-axis, while the doses of 5.0 mg/kg is plotted as 0.20 on the X-axis and 6.00 on the Y-axis. A regression line Y of these three points is obtained as follows:

$$i\ Y = a + bX = 3.1658 + 16.0366X,$$

whereby a correlation coefficient $r = 0.999$ is applied. The intersection of the Y-line and the Y-axis shows 1/RMAX and hence the index RMAX is represented by the inverse number of a, as $1/a = 0.32$ mg/kg/min.

In accordance with a two-point analysis method of 0.5 mg/kg and 5.0 mg/kg, the index RMAX is calculated from a regression line $Y = 2.7544 + 16.2278X$, applying Lineweaver-Burk plotting, as 0.35 mg/kg/min.

In the aforementioned method of measuring the index RMAX, however, some conditions are required in theory of adaptation, while errors may be caused from various sources in the process of measurement and calculation. For example, impossible minus measurement values are recognized once in a while. Further, when the dose quantity is changed three times for measuring the index RMAX as hereinabove described, intravenous injection must be made fifteen times, blood must be collected four times, and ICG must be injected three times, which imposes undesirable burdens on the patient, while several days are required for the pretesting.

SUMMARY OF THE INVENTION

Accordingly, a principal object of the present invention is to provide a liver function testing apparatus which can reduce mental and physical burdens on a testee, to automatically measure an index expressing the total amount of hepatic cell function.

Another object of the present invention is to provide a liver function testing apparatus which can rather very simply and automatically measure an index expressing the total amount of hepatic cell function, while requiring an injection of ICG only once.

Still another object of the present invention is to provide a liver function testing apparatus which can automatically select a prescribed light source in response to the dose quantity of a specific dye to measure an index expressing the total amount of hepatic cell function.

A further object of the present invention is to provide a liver function testing apparatus which can eliminate the influence of such factors as blood flow disturbance, vibration of an organism and pulsation in the organism, when a sensor is attached to the organism by performing biocalibration prior to a measurement.

Briefly stated, vital tissue is exposed to a first light signal having a wavelength absorbed by a specific dye dosed into the blood of the vital tissue, to be taken in and removed by the liver, and to a second light signal having a wavelength not absorbed by the specific dye. First and second photoelectric conversion signals corresponding to the first light signal and to the second light signal obtained from the vital tissue, are sampled so that a coefficient of a regression line expression between the first and second photoelectric conversion signals is determined on the basis of variable components in the blood included in the sampled first and second photoelectric conversion signals to perform a biocalibration. A value correlated with a specific dye concentration in the blood determined on the basis of a sampling signal during a prescribed period of time after an injection of the specific dye and the determined coefficient of the regression line expression are processed to obtain a coefficient of a simulation function as a function of time by applying the method of least squares, thereby to obtain an index RMAX expressing the total amount of hepatic cell function.

Thus, according to the present invention, the index RMAX expressing the total amount of hepatic cell function can be measured by giving an ICG injection only once without any taking of blood samples which is quite contrary to the conventional case, whereby mental and physical burdens on a testee can be much reduced. Further, adverse factors such as blood flow disturbance, vibration of an organism, pulsation in the organism, and change of the blood volume in the organism when a sensor is attached to the organism are avoided or at least prevented from interfering with a correct measurement.

In a preferred embodiment of the present invention, light source means are formed by a plurality of first light sources for exposing vital tissue to first light signals of different wavelengths which are absorbed by specific dyes, and second light source means for exposing the vital tissue to a second light signal of a wavelength which is not absorbed by any specific dye. Input means is provided to input the dose quantity D (mg/kg) of each of different specific dyes, so that a corresponding light source is selected from the plurality of first light source means in response to a currently inputted dose quantity, to apply light from the selected light source to the vital tissue as a first light signal.

Thus, according to the preferred embodiment of the present invention, a prescribed light source can be automatically selected in response to the dose quantity of a specific dye, whereby the measurement can be performed with the same accuracy for any specific dye of any dose quantity, to effectively measure the index RMAX expressing the total amount of hepatic cell function.

In a more preferred embodiment of the present invention, a blood plasma disappearance rate k and a liver removal ratio $R = D \times k$ are evaluated on the basis of an obtained coefficient of a simulation function wherein k is said disappearance rate, R is indicated as mg/kg/min and D is a dye dosing value in mg of dye per kg of patent weight.

Thus, in a further preferred embodiment of the present invention, the blood plasma disappearance rate k and the removal ratio R are obtained while processing the blood plasma disappearance rate k and the liver removal ratio R is performed a plurality of times by changing respective dose quantities of different specific dyes, thereby to obtain the index RMAX expressing the total amount of hepatic cell function on the basis of the plurality of dose quantities and removal ratios R thus obtained.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 1 to 4 are diagrams for illustrating the principle of biocalibration employed in the present invention;

FIGS. 8A to 8E are flow charts for concretely illustrating the operation of the embodiment of FIG. 5, in which FIG. 8A shows a data sampling subroutine, FIG. 8B shows a biocalibration mode, FIG. 8C shows an initialization mode and FIGS. 8D and 8E show a measurement mode;

DESCRIPTION OF THE PREFERRED EMBODIMENTS

Before explaining embodiments of the present invention, description is now made on the principle of biocalibration employed in the present invention with reference to FIGS. 1 to 4.

The symbol I1 indicates a first light quantity having a wavelength $\lambda 1$ which is largely absorbed by a specific dye. I2 indicates a second light quantity having a wavelength $\lambda 2$ which is not absorbed by the specific dye. The light quantities I1 and I2 are incident upon the vital tissue 15. The symbols L1 and L2 indicate light quantities after passage through a prescribed optical path in the vital tissue. The relationships between the incident light or entering quantities I1 and I2 and the exiting light quantities L1 and L2 when a specific dye has been injected, are as follows:

$$\log I1/L1 = kg1 \cdot Cg \cdot Vb - f1(Cb, Vb) - \gamma t1 \tag{1}$$

$$\log I2/L2 = f2(Cb, Vb) - \gamma t2 \tag{2}$$

Respective coefficients and variables are shown in FIG. 1. Symbols f1 and f2 represent functions which are determined by blood characteristics at the wavelengths $\lambda 1$ and $\lambda 2$.

On the other hand, relations between the incident light quantities I1 and I2 and the passing light quantities L1 and L2 before injection of the specific dye are as follows:

$$\log I1/L1 = f1(Cb, Vb) + \gamma t1 \tag{3}$$

$$\log I2/L2 = f2(Cb, Vb) + \gamma t2 \tag{4}$$

Figure 3:
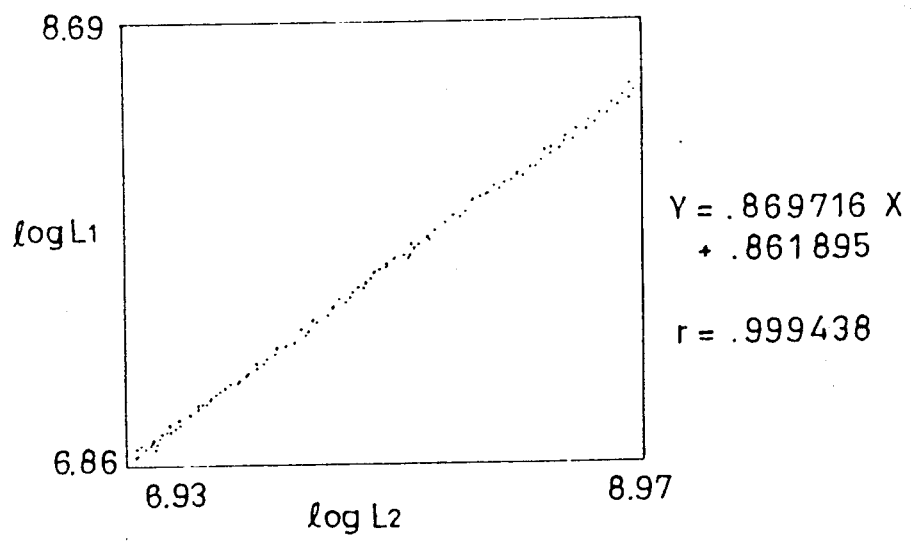

The relationship between the passing light quantities L1 and L2 prior to an actual injection of the specific dye, is measured as shown in FIG. 2. The relationship is a linear relationship as shown in FIG. 3. The data represented in FIG. 3 are obtained by attaching a sensor to an organism and fluctuating the blood volume in the organism. It has been confirmed that such linearity is reproducible without any individual difference. Then, the above expressions (3) and (4) would can be rewritten as follows:

$$\log L1 = A \log L2 + B \tag{5}$$

That is, the same can be expressed as follows, by using the expressions (3) and (4):

$$\log I1 - \{f1(Cb, Vb) + \gamma t1\} = A[\log I2 - \{f2(Cb, Vb) + \gamma t2\}] + B \tag{6}$$

where Cb represents a blood concentration in a sample and Vb represents a blood volume in the sample.

A function C obtained by multiplying the concentration of the specific dye by the blood volume in the sample and the absorption coefficient of the specific dye by using the expressions (1) and (2) after injection of the specific dye, can be expressed as follows:

$$C = \log L1 - [A \cdot \log L2 + B] \tag{7}$$

The function C is found by the expression (7) as follows:

$$C = \log I1 - kg \cdot Cg \cdot Vb - f1(Cb, Vb) + \gamma t1 \\ - A[\log I2 - \{f2(Cb, Vb) + \gamma t2\}] - B \tag{8}$$

Through the expression (6), we have:

$$C = -kg \cdot Cg \cdot Vb \tag{9}$$

Hence, it is understood that a signal of the function C can be obtained by using FIG. 3 as a calibration curve.

However, for the function C, although the coefficient kg is constant, it can be considered that the blood volume Vb in each part is changed from time to time, and hence, if the blood volume Vb in a prescribed sample created by the sensor once attached is changed, the amount of the specific dye is also changed in proportion thereto although the dye concentration remains unchanged. This is typically shown in FIG. 4.

Figure 4:
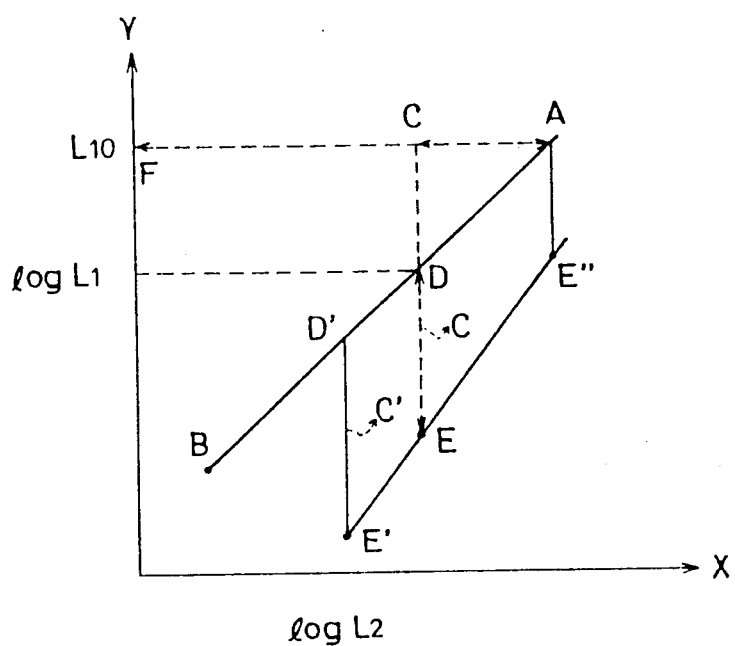

Referring to FIG. 4, it is assumed that DE represents the value of the function C after a lapse of t1 in minutes. The blood contained in the prescribed sample obtained after a lapse of $t1 + \Delta t$ minutes is changed in volume, whereby an observation point is changed from E to E'. Assuming that $\Delta t$ is sufficiently less than one minute, the specific dye concentration in the blood after the lapse of t1 minutes may be considered identical to that after the lapse of $t1 + \Delta t$ minutes. However, as to the function C, the change is from C=DE to C'=D'E'. $C \neq C'$, and hence some correction must be performed. By normalizing DE and D'E' at a point L10, an apparent fluctuation of the dye concentration due to the fluctuation of the blood volume, can be corrected.

When the specific dye is injected, signal of logL1 only fluctuates to a point E, for example. At this time, DE becomes the function C as shown in the expression (9). The blood volume Vb in the expression (9) can be interpreted as being denoted by CD, and hence, normalizing the Y coordinate of a point A as L10, the same is expressed as follows:

$$Vb \propto 1 - \frac{\log L10 - (A \cdot \log L2 + B)}{\log L10} \tag{10}$$

Hence, a signal Cg corresponding to the specific dye concentration can be found by the expressions (7) and (10) as follows:

$$Cg = \frac{\log L_{10}[\log L_1 - (A \cdot \log L_2 + B)]}{2\log L_{10} - (A \cdot \log L_2 + B)} \tag{11}$$

Using the method of least squares, the function Cg of a simulation curve in time change of the aforementioned result Cg of calculation is expressed as follows:

$$Cg = Ae^{-Bt} \tag{12}$$

where t represents the elapsed time after injection of the specific dye and symbols A and B represent constants.

The constants A and B are found by the above expression (12). The blood plasma disappearance rate k and the liver removal ratio R are expressed as follows:

$$k = B \tag{13}$$

$$R = K \cdot D \tag{14}$$

Then D is the dose quantities of a specific die in mg of dye per kg of patient weight.

While the biocalibration employed in the present invention has been described in the above, description is now made on an embodiment of the present invention employing the aforementioned biocalibration.

Figure 5:
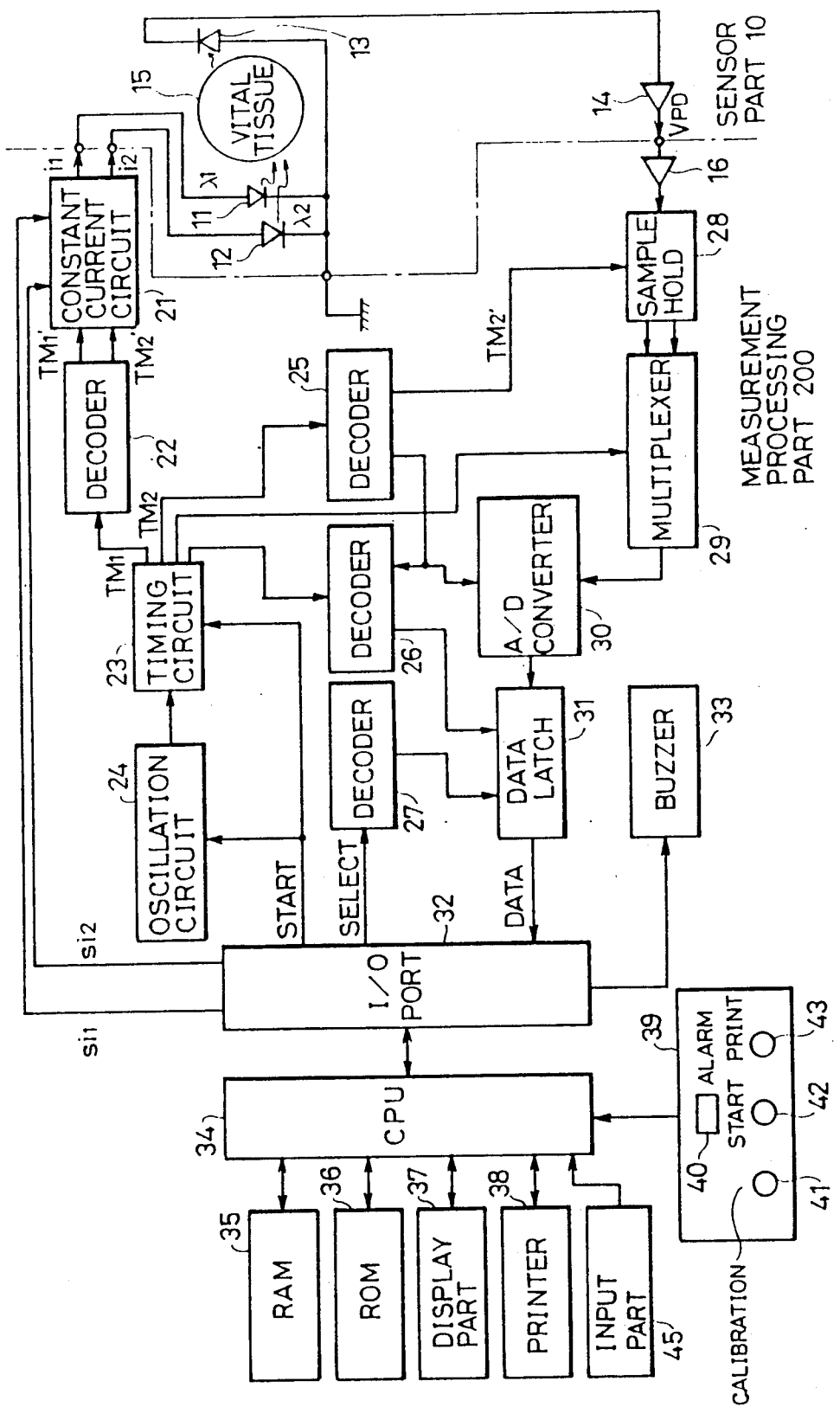
FIG. 5 is a schematic block diagram showing the entire structure of an embodiment of the present invention.

Referring to FIG. 5, the present liver function testing apparatus comprises a sensor part 10 and a measurement processing part 200. The sensor part 10 includes a first light source 11, a second light source 12, a light receiving element 13 and a preamplifier 14. The first light source 11 generates optical pulses or light signals of a wavelength $\lambda 1$ having a large absorbance to a specific dye. The light source 12 generates optical pulses or light signals of a wavelength $\lambda 2$ having a small absorbance. The light receiving element 13 receives light applied to vital tissue 15 from the light sources 11 and 12 to pass through a prescribed optical path through the tissue 15. The light sources 11 and 12 are driven by the measurement processing part 200 to alternately emit light by pulse operation, respectively.

Figures 6, 7:
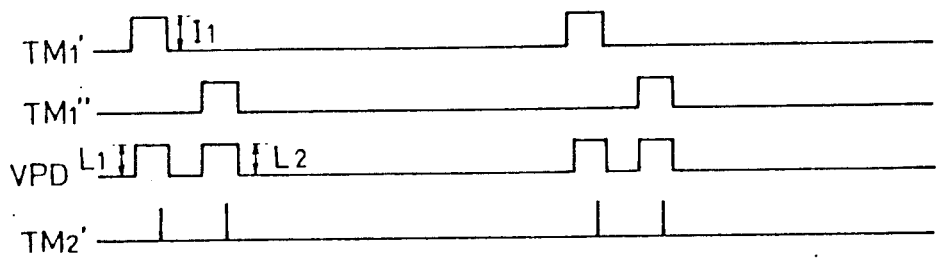
FIG. 6 illustrates the timing for detecting quantities of light signals having wavelengths $\lambda 1$ and $\lambda 2$ after passage through a prescribed or defined optical path in a measured object.
FIG. 7 illustrates data stored in a RAM as shown in FIG. 5.

The measurement processing part 200 includes a CPU 34 which serves as arithmetic means. The CPU 34 supplies a start signal to an oscillation circuit 24 and to a timing circuit 23 through an I/O port 32. The oscillation circuit 24 produces a prescribed clock signal. This clock signal and the aforementioned start signal are utilized to supply a constant currents i1 to the first light source 11, and a constant current i2 to the second light source 12, from a constant current circuit 21 through the timing circuit 23 and a decoder 22 at timing TM1' and TM1" as shown in FIG. 6.

The light l1 emitted from the first light source 11 and the light l2 emitted from the second light source 12 pass through the prescribed optical path in the vital tissue 15, to be incident upon the light receiving element 13. A current generated from the light receiving element 13 is supplied to the preamplifier 14 performing a current-to-voltage conversion, and amplifying the signal to be supplied to the measurement processing part 200. Output of the preamplifier 14 is amplified to a level within a prescribed range by an amplifier 16 provided in the measurement processing part 200, whereby an output such as VPD shows in FIG. 6 is obtained. A sample and hold circuit 28 samples and holds the output from the amplifier 16 on the basis of a timing signal TM2', shown in FIG. 6, generated by the timing circuit 23 and a decoder 25.

The signal thus sampled and held is selected by a multiplexer 29 and converted into a digital signal by an A-D converter 30, to be data-latched by a data latch 31. At this time, the multiplexer 29, the A-D converter 30 and the data latch 31 are controlled in timing by the timing circuit 23 and the decoder 26.

The latched data are timed by a decoder 27 through a select signal outputted from the CPU 34 through the I/O port 32, for storing in a RAM 35 as digital signals L1 and L2. The I/O port 32 is connected with a buzzer 33, which a reminder or timing signal for injecting the specific dye. Further, the CPU 34 is connected with the RAM 35, a ROM 36, a display part 37, a function part 39, and an input part 45. The RAM 35 is adapted to store data as shown in FIG. 7 as hereinafter described, and the ROM 36 stores programs based on flow charts shown in FIGS. 8A to 8E as hereinafter described. The display part 37 displays data as shown in FIGS. 9 to 12, as hereinafter described. A printer 38 is adapted to print the result of a liver function test.

The function part 39 includes an alarm LED 40, a calibration key 41, a start key 42 and a print key 43. The alarm LED 40 is adapted to display an alarm when the reliability of the test result is small. The calibration key 41 is adapted to set a biocalibration mode. The start key 42 is adapted to start a measurement mode. The print key 43 is adapted to command a printout of the test result. The input part 45 is adapted to input the dose quantity of a specific dye.

In the aforementioned exemplary structure shown in FIG. 5, the light emitted from the first and second light sources 11 and 12 to pass through the prescribed optical path in the vital tissue 15, is received by a single light receiving element 13. However, the invention is not restricted to this example. Rather, light receiving elements may be provided in correspondence to the first and second light sources 11 and 12 respectively to sample outputs of the respective light receiving elements, thereby to read the respective sampling outputs by the CPU 34 in a time-sharing manner. Alternatively, a single light source commonly emitting light having a wavelength λ1 absorbed by specific dye and light having a wavelength λ2 not absorbed by the same may be provided as light source means, with provision of two filters for individually transmitting the light of the respective wavelengths and light receiving elements corresponding to the respective ones of the filters.

Figure 11:
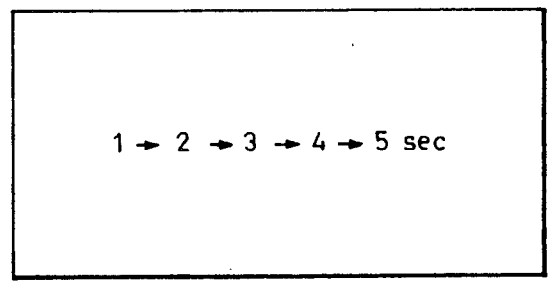
Figure 12:
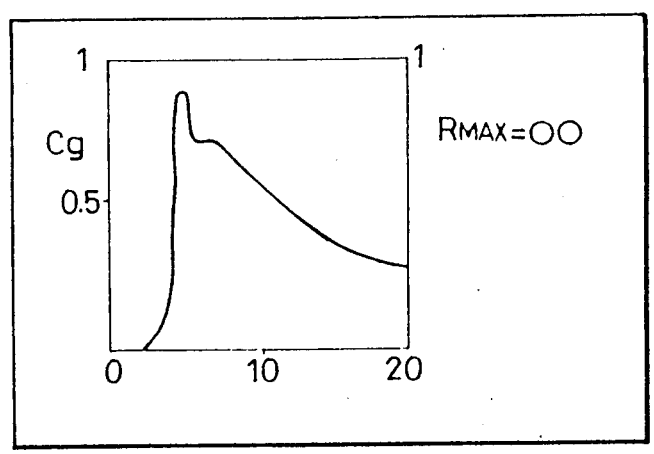
Figure 13:
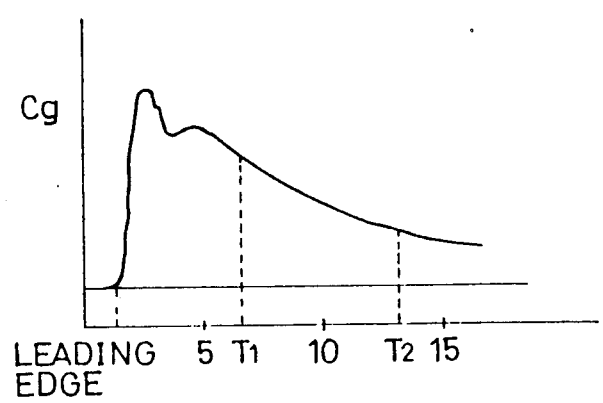
FIG. 13 shows an example of a disappearance curve of specific dye measured in the present invention.

FIG. 7 illustrates data stored in the RAM 35 as shown in FIG. 5, and FIGS. 8A to 8E are flow charts for illustrating a concrete operation of the embodiment of the present invention, while FIGS. 9 to 12 are illustrative of exemplary displays on the display part 37 shown in FIG. 5 in FIG. 13 is illustrative of an exemplary disappearance curve of a specific dye and the result of RMAX measured in the present invention.

With reference to FIGS. 5, 8A to 8D and 13, the operation of the embodiment of the present invention will now be described. The operation of the present apparatus includes a data sampling mode, a biocalibration mode, an initialization mode, and a measurement mode, and FIGS. 8A, 8B, 8C, 8D and 8E show operation flow charts of these modes, respectively.

Figure 8A:
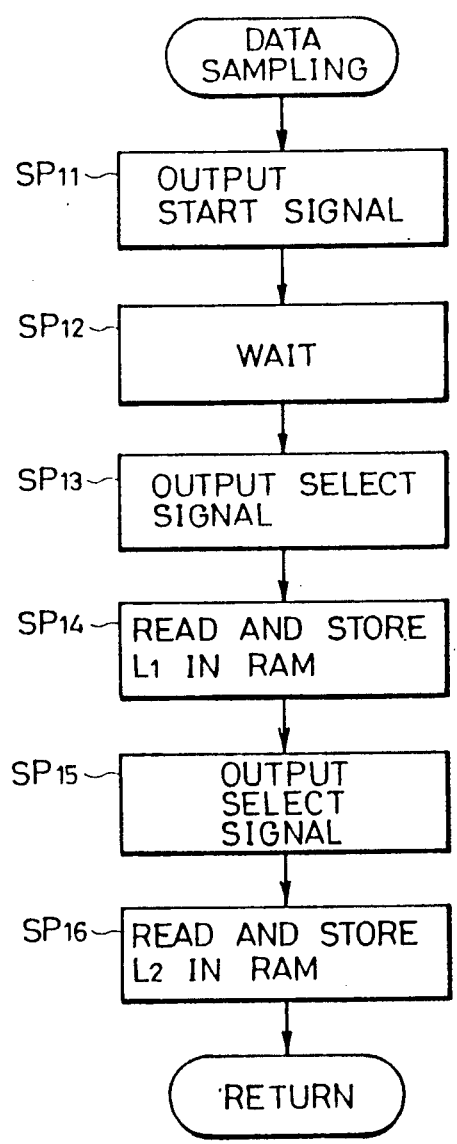

First, it is pointed out that the data sampling mode shown in FIG. 8A is executed as subroutines in the biocalibration mode and the measurement mode as hereinafter described. Steps, abbreviated as SP in the figures, SP11 to SP16 are adapted to sample quantities of light of a pair of wavelengths λ1 and λ2 after passage through a measured object and store the same in the RAM 35. Namely, the CPU 34 outputs the start signal through the I/O port 32 shown in FIG. 5 at the step SP11. The values L1 and L2 are data-latched by the start signal, as hereinabove described. The CPU 34 waits until the data are latched at the step SP12.

Then, at the step SP13, the CPU 34 outputs the selected signal to a selected line shown in FIG. 5 through the I/O port 32, to read the data of L1 through the I/O port 32 at the step SP14, thereby to store the same in a storage area 8a1 of the RAM 35 as shown in FIG. 7. Similarly, the CPU 34 stores the data of L2 in a storage area 8a2 of the RAM 35 at the steps SP15 and SP16. Upon completion of the aforementioned operation at the step SP16, the CPU 34 returns to the original step. This will be described with reference to FIG. 8B showing the biocalibration mode and FIGS. 8D and 8E showing the measurement mode.

Figure 8B:
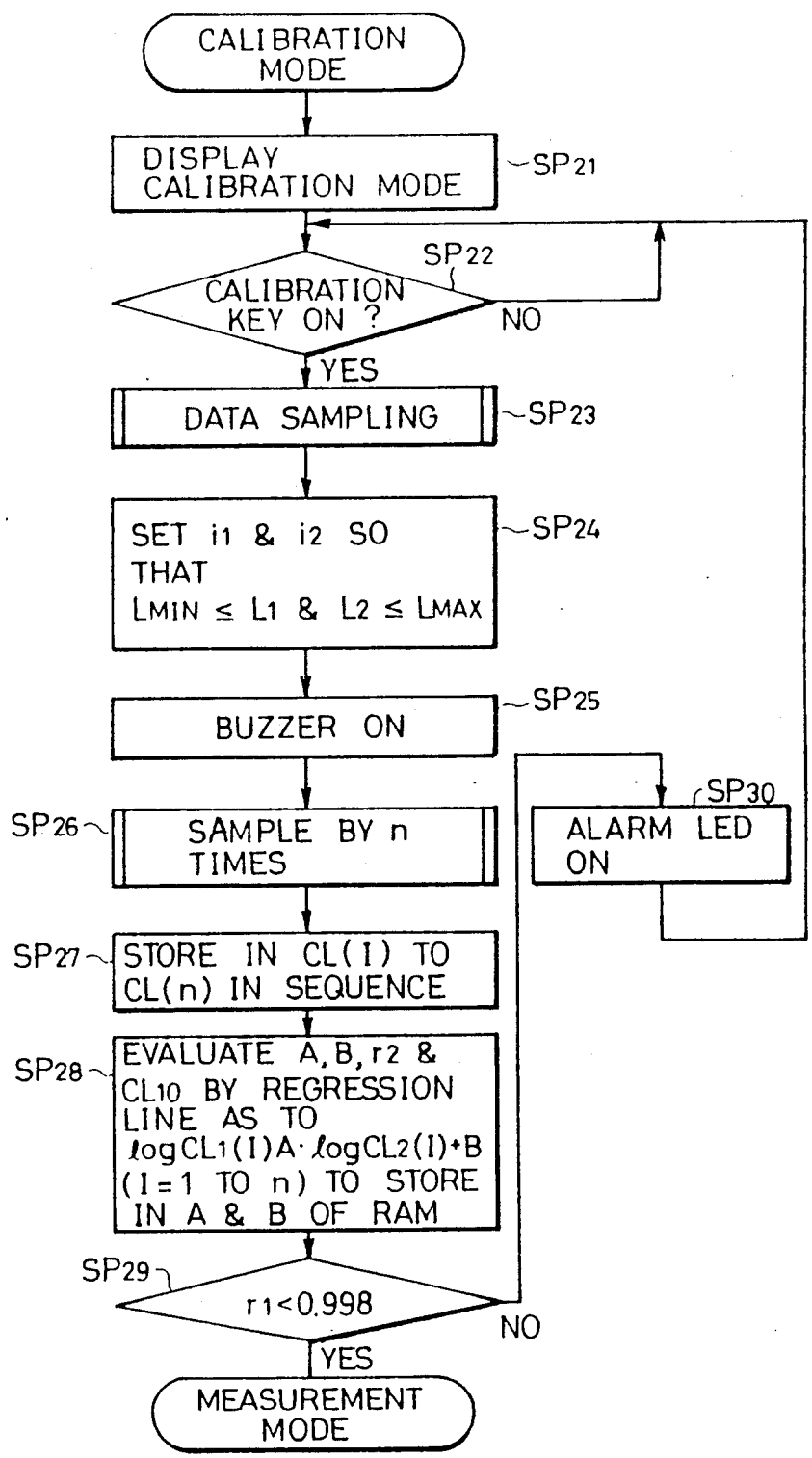
Figure 8D:
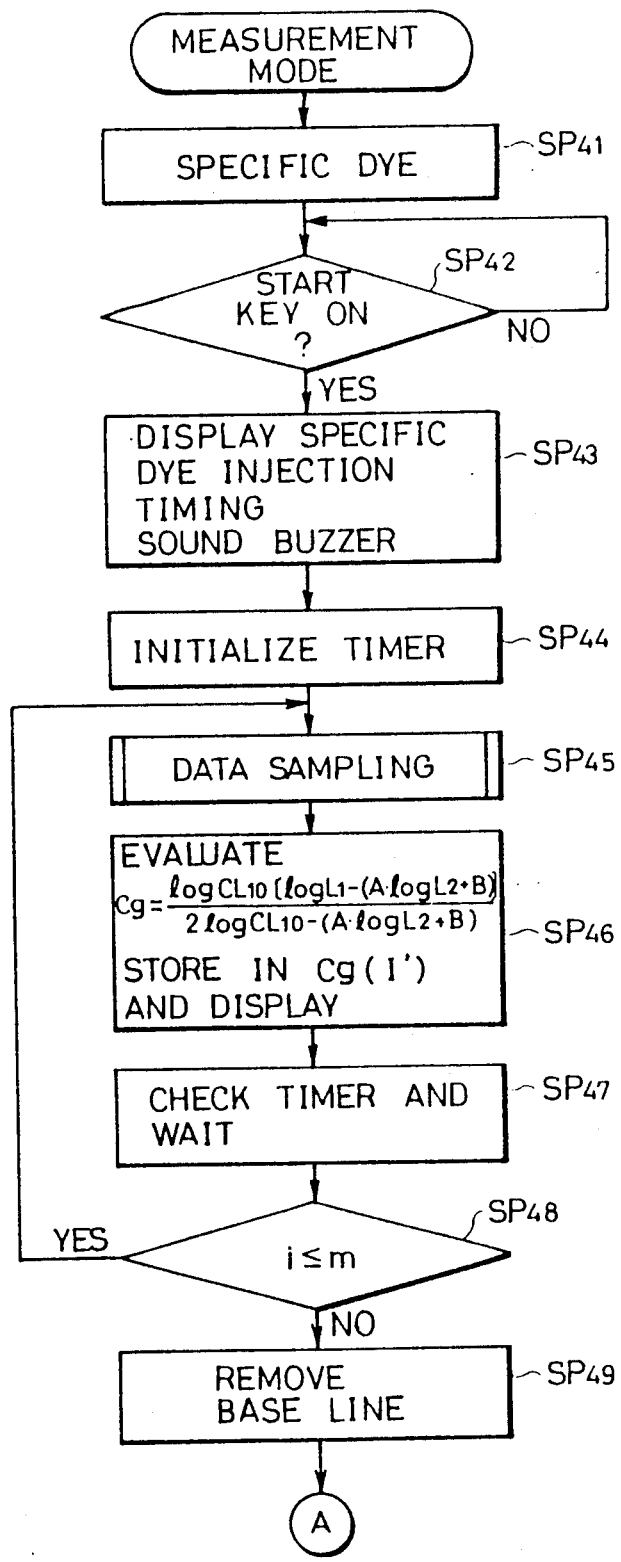
Figure 8E:
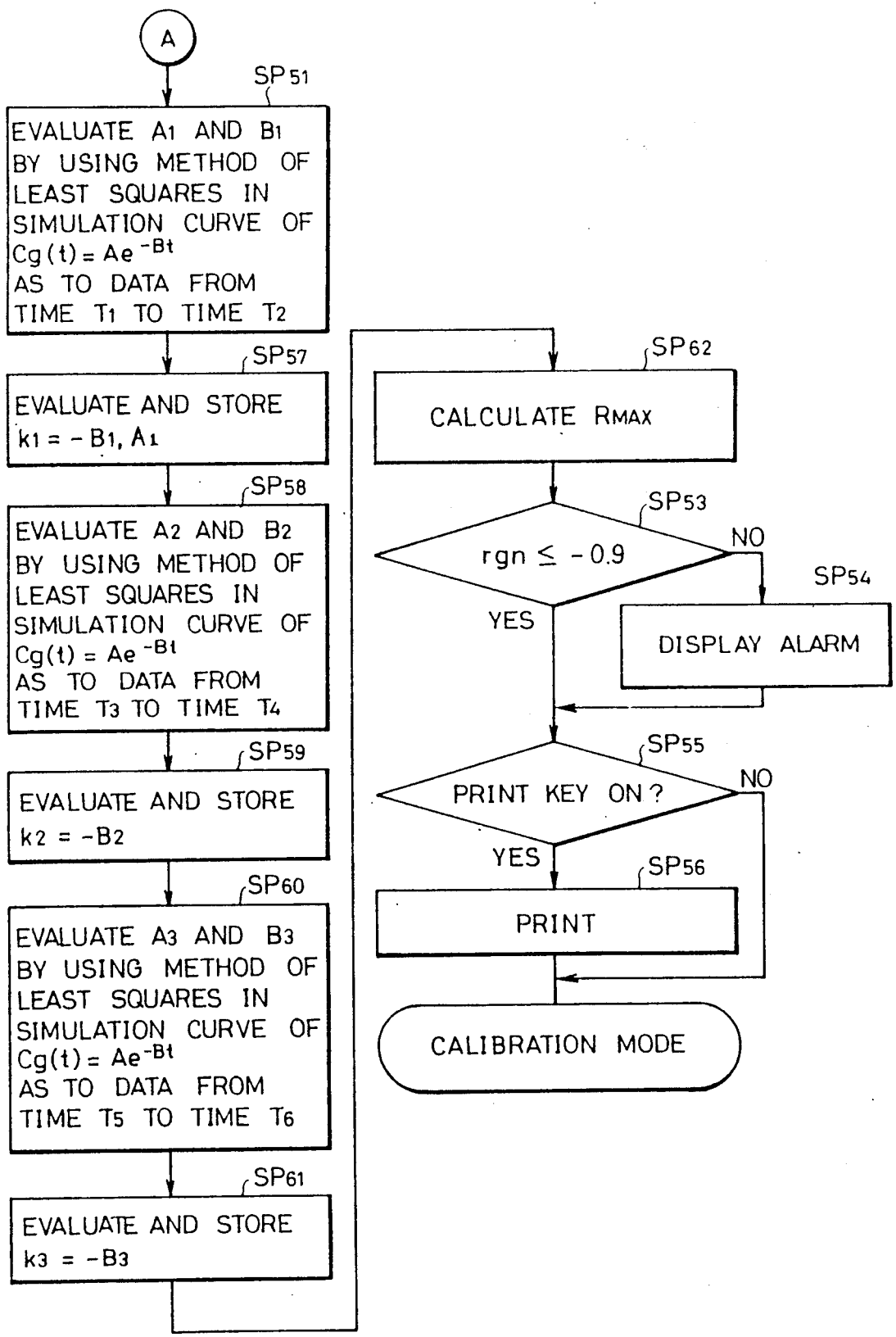
Figure 9:
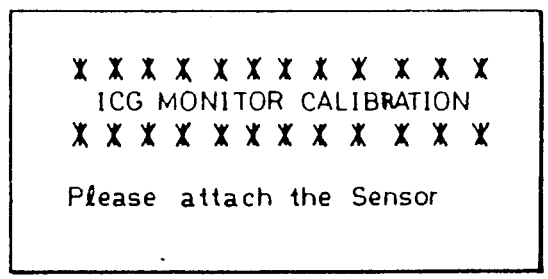
FIGS. 9 to 12 are illustrative of exemplary displays on a display part as shown in FIG. 5.

FIG. 8B shows the operation flow chart of the biocalibration mode, which is started when power is supplied to the apparatus or upon completion of the operation of the measurement mode shown in FIGS. 8D and 8E, as hereinafter described. At a step SP21, the CPU 34 makes the biocalibration mode appear on the display part 37. This display shows that the apparatus enters the biocalibration mode and indicates that should now be the sensor part 10 attached to a tissue 15, as shown in FIG. 9, for example. In accordance with this indication, an operator attaches the sensor part 10 to the vital tissue 15.

Thereafter the CPU 34 waits until the calibration key 41 is operated at a step SP22. When the calibration key 41 is operated, the CPU 34 advances to a step SP23, to execute the data sampling subroutine shown in FIG. 8A, as hereinabove described.

Then, the CPU 34 controls the constant current circuit 21 so that the data L1 and L2 read at the step SP23, are within ranges of light quantity data LMAX and LMIN stored in storage areas 8b1 and 8b2 of the RAM 35. The CPU 34 then stores current set values i1 and i2 in storage areas 8c1 and 8c2 in the RAM 35. Thereafter the currents i1 and i2 regularly flow to the light sources 11 and 12. Initializing operation for the aforementioned currents will be described in further detail with reference to FIG. 8C.

Then, the CPU 34 sounds the buzzer at a step SP25, to inform that power setting is completed. Subsequent steps SP26 to SP29 are shown in the flow chart for performing the aforementioned biocalibration. In more concrete terms, the CPU 34 samples the values of L1 and L2 n times respectively, at the steps SP26 and SP27, to cause CL1(1) to CL1(n) to be stored in storage areas 8d1 to 8dn and CL2(1) to CL2(n) stored in storage areas 8e1 to 8en. At the subsequent step SP28, the CPU 34 performs regression line analysis with respect to logCL-1(I) and logCL2(I) (I=1 to n), in accordance with the following operation expression:

$$\log CL1(I) = A \cdot \log CL2(I) + B$$

The CPU 34 finds the values A and B in the above operation expression, a correlation coefficient r1 and the maximum value of CL1(I) (I=1 to n) as CL10, to store the same in storage areas 8f1, 8f2, 8f3 and 8f4 in the RAM 35 respectively.

Then, at the step SP29, the CPU 34 determines whether or not the correlation coefficient r1 is at least 0.998 in order to verify the reliability of the biocalibration, advances to a step SP30 if the same is less than 0.998 to light the alarm LED 40, and returns to the step SP22 to again perform a biocalibration. On the other hand, if a determination is made that the correlation coefficient r1 is at least 0.998, the CPU 34 advances to the measurement mode as shown in FIG. 8D and 8E. The reference value 0.998 of the correlation coefficient r1 herein employed is a mere example, which is determined by performance of the entire apparatus. During the data sampling of that takes place n times at the step SP26, the testee raises and brings down his hand and presses the same by the sensor, in order to change the blood volume in the organism.

Figure 8C:
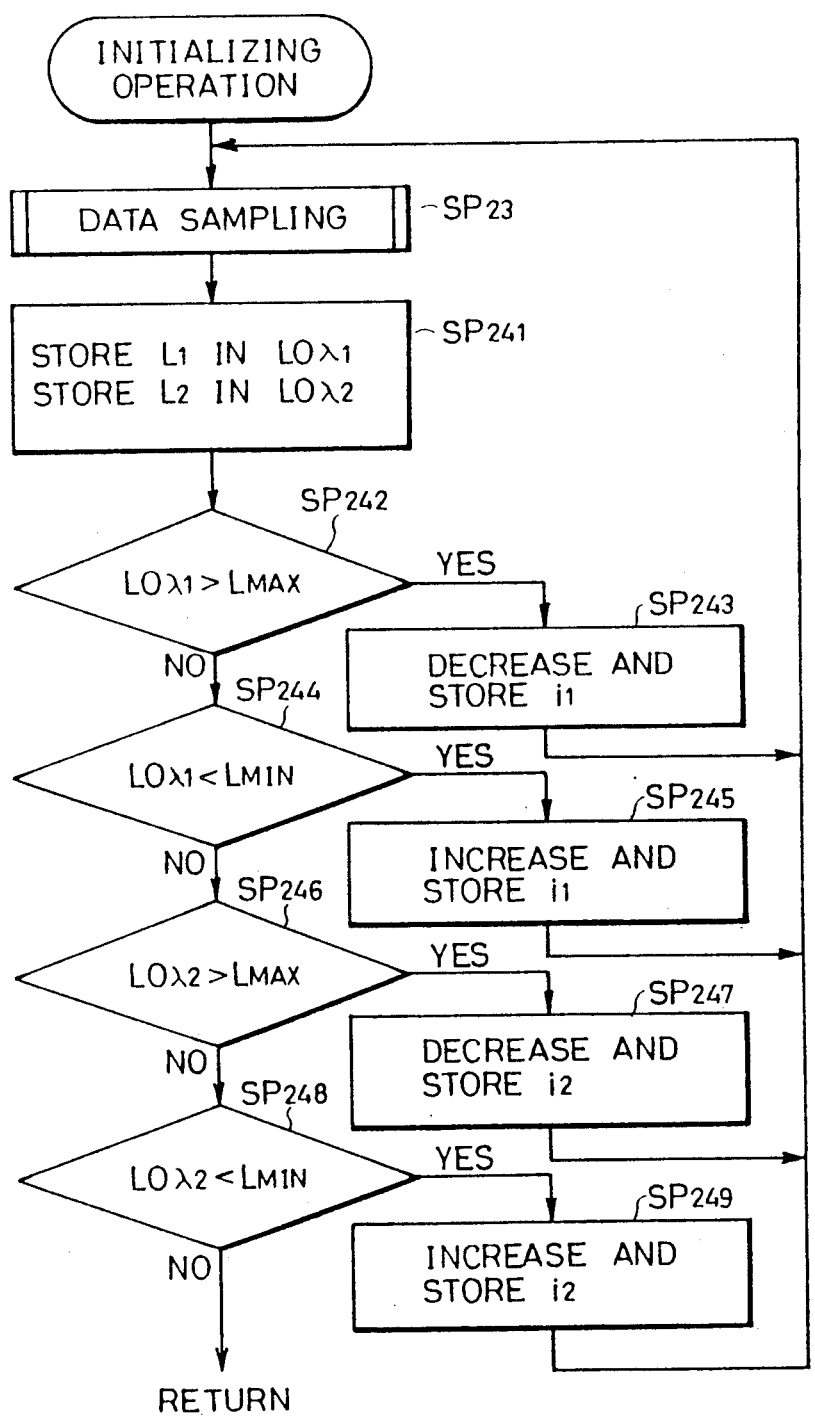

With reference to FIG. 8C, the aforementioned initializing operation at the step SP24 as shown in FIG. 8B will now be described in more detail.

The light quantity data L1 and L2 of the light of the wavelengths λ1 and λ2 are stored in the storage areas 8a1 and 8a2 of the RAM 35. At a step SP241, the CPU 34 stores the values of L1 and L2 in storage areas 8h1 and 8h2 in the RAM 35 as L0λ1 and L0λ2 respectively. Then the CPU 34 executes steps SP242 to SP249, to adjust the set values of the currents flowing from the constant current circuit 21 so that L0λ1 and L0λ2 are set between the light quantity data LMAX and LMIN (LMAX>LMIN) stored in the storage areas 8b1 and 8b2 of the RAM 35.

More specifically, of L0λ1 is greater than LMAX at the step SP242, the CPU 34 advances to the step SP243 to set the current set value i1 at a small value to again execute the steps SP23 and SP241, and a determination is again made as to whether or not L0λ1 is greater than LMAX at the step SP242. If L0λ1 is less than LMAX, the CPU 34 advances to the step SP244 to determine whether or not L0λ1 is less than LMIN. If L0λ1 is less than LMIN, the CPU 34 increases the value of the current set value i1 at the step SP245, to return to the aforementioned step SP23. This operation is repeated to fix the current set value i1 so that L0λ1 is between LMAX and LMIN.

Then, at the steps SP246 to SP249, the current set value i2 is fixed so that L0λ2 is between LMAX and LMIN, similarly to the steps SP242 to SP245. Thus, the current set values i1 and i2 finally set at the steps SP23 to SP249 are stored in the storage areas 8c1 and 8c2 of the RAM 35.

Figure 10:
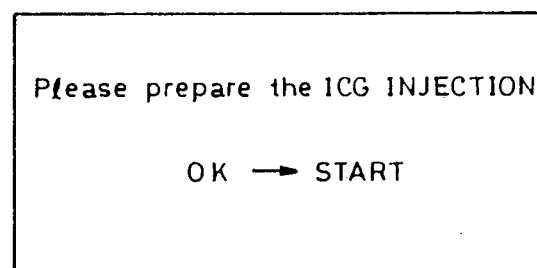

The measurement mode will now be described with reference to FIGS. 8D and 8E. At a step SP41, the CPU 34 displays on display 37 an instruction to prepare the injection of the specific dye as shown in FIG. 10. In accordance with the display, the operator prepares for the injection of the specific dye into the testee. At this time, the input part 45 inputs the dose quantity of the specific dye, e.g., 2 mg/kg as D1, which is stored in a storage area 8j of the RAM 35.

At a step SP42, the CPU 34 waits until the start key 42 is operated. Upon a determination that the start key 42 has been operated, the CPU 34 displays a timing signal for injecting the specific dye at a step SP43, while sounding the buzzer 33. This is displayed as 1→2→3→4→5 as shown in FIG. 11, for example, so that the measurer injects the specific dye upon display of "5". The CPU 34 generates a first sound by the buzzer 33 with the displays of "1", "2", "3", and "4", while generating a different sound by the buzzer 33 upon display of "5".

Upon generation of the sound and the display, the measurer injects the specific dye. The CPU 34 sets "0" as the initial value of a timer at a step SP44. Then, at a step SP45, the CPU 34 executes a data sampling program, which is the subroutine as hereinabove described with reference to FIG. 8A. Then, the sampling data are stored in the storage areas 8a1 to 8a2 of the RAM 35 as L1 to L2, respectively.

At a step SP46, the CPU 34 performs processing operation based on the following operation expression by using the coefficients A, B and CL10 stored in the storage areas 8f1, 8f2 and 8f4 of the RAM 35 in the biocalibration mode as hereinabove described with reference to FIG. 8B, to store Cg(I) in a storage area 8g1 to 8gm of the RAM 35:

$$Cg(I) = \frac{\log CL_{10}[\log L_1(I) - (A \cdot \log L_2(I) + B)]}{2\log CL_{10} - (A \cdot \log L_2(I) + B)}$$

The value of Cg(I) is displayed on the display part 37 at the step SP46 in a mode shown in FIG. 12, for example. Referring to FIG. 12, the abscissa indicates the elapsed time from the injection of the specific dye and the ordinate indicates the value of Cg(I). If m represents the sampling number of a disappearance curve of the specific dye, if I indicates integers 1 to m, and Ts represents a measured time of the disappearance curve, then a single sampling time is ITM=Ts/(m−1). The same coincides with the injection time of the specific dye if I=1. At a step SP47, the CPU 34 waits during this sampling time ITM in a standby state.

Upon a lapse of this standby time, the CPU 34 judges whether or not i is greater than m at a step SP48. The CPU 34 advances to a step SP49 if i is greater than m, while the same again returns to the step SP45 to repeat sampling if the former is less than the latter. The data Cg(I) stored in the storage areas 8g1 to 8gm of the RAM 35 trace a disappearance curve of the specific dye as shown in FIG. 13, for example, and the leading edge thereof is detected so that data preceding the same are subtracted as baselines from the respective values of Cg(I) at a step SP49, to be again stored in the storage areas 8g1 to 8gm. The values for L1 to L2 at the step SP45 may be average values of k times, in order to improve the accuracy of the measurement.

Then, at a step SP51, the CPU 34 finds the constants A1 and B1 by using the method of least squares in a simulation curve of:

$$Cg(I) = A1 \cdot e^{-B1I}$$

$$I = Ts/(m-1) \ (min.)$$

with respect to data between times T1 to T2 (0<T-1<T2 <Ts) within the data Cg(I) stored in the storage areas 8g1 to 8gm.

At a step SP57, the CPU 34 evaluates K1 from K1=−B1 while evaluating a correlation coefficient rg1, to store the same in storage areas 8k1 and 8k2 of the RAM 35. Similarly, the CPU 34 evaluates constants A2 and B2 in a block between times T3 and T4 at a step SP58, and evaluates a coefficient K2 and a correlation coefficient rg2 at a step SP59 to store the same in the storage areas 8k3 and 8k4. The CPU 34 further processes constants A3 and B3 in a block between times T5 and T6 at a step SP60, and evaluates a coefficient K3, and a correlation coefficient rg3 at a step SP61, to store the same in the storage areas 8k5 and 8k6. Then the CPU 34 processes the index RMAX at a step SP62.

Figure 14:
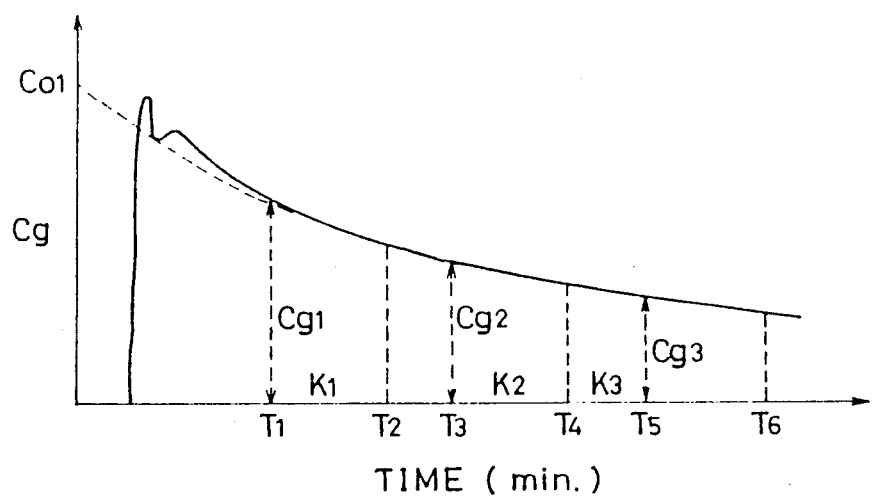
FIGS. 14 to 16 are diagrams for illustrating the operation for measuring an index RMAX according to the present invention.
Figure 15:
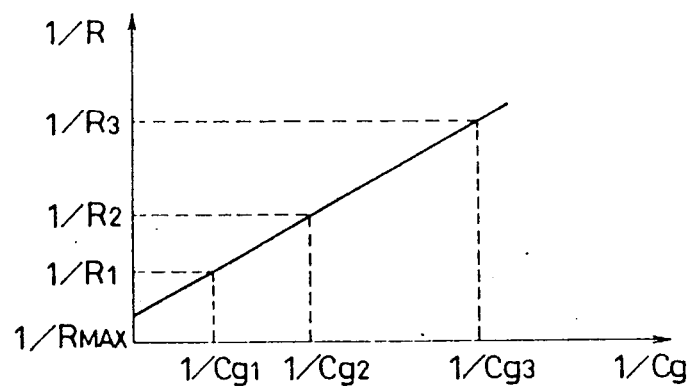

The times T1 to T6 and the coefficients K1 to K3 are mapped in their relationship as shown in FIG. 14. The CPU 34 knows that Cg1, Cg2 and Cg3 represent values corresponding to specific dye concentration values at the times T1, T3 and T5. The CPU 34 further knows that Ri=Cgi×Ki for displaying the graph shown in FIG. 15. Referring to FIG. 15, the abscissa is indicated by 1/Cg and the ordinate is indicated by 1/R. On the basis of these data, the CPU 34 processes regression analysis coefficients a and b by using the method of least squares, through the following operation expression:

$$1/Ri = a(1/Cgi) + b$$

, wherein i=1, 2, ..., m, m≧2, where i=1 is a first time block, and "a" and "b" are said regression analysis coefficients.

Then, the CPU 34 processes the index RMAX and rMAX in accordance with the following operation expression, to store the same in the storage areas 8/1 and 8/2 of the RAM 35:

$$RMAX = 1/b.$$

YMAX is the coefficient of correlation.

Although three times blocks are provided in the above embodiment, such time blocks may have any number provided at least two time blocks are used. The accuracy is improved as the number of times blocks is increased.

Although 1/Cg1, 1/Cg2 and 1/Cg3 are plotted along the abscissa in FIG. 15, this is a simplified type and the index RMAX can be more correctly measured by evaluating the coefficient A1 on the basis of the following operation expression wherein the coefficient A1 becomes a coefficient C01, thereby to create the data as shown in FIG. 14. If T1=5 min. and the dose of ICG is D1 in mg/kg, C01 may correspond to D1, D2 may be equal to D1·Cg2/C01 and D3 may be equal to D1·Cg3/C01, where Ri=Di×Ki. D1 is set at 2 mg/kg, for example, as a value specific to the apparatus, or it may be inputted through the input part 45.

Then, at a step SP53, the CPU 34 determines whether or not a correlation coefficient rgn is less than 0.95, for example, to check the degree of correlation, since correlation is improved as the correlation coefficient rgn approaches −1. However, a value −0.95 is a provisional value between zero to −1, and the reliability of the apparatus is improved as the value approaches −1.

The CPU 34 determines that the reliability is small, if the correlation coefficient rgn is greater than 0.95, for example, to turn on the alarm LED 40 at a step SP54. When the CPU 34 determines that the correlation coefficient rgn is less than −0.95, for example, and the measurement is reliable at the step SP53, on the other hand, the CPU 34 advances to a step SP55 without flashing the alarm LED 40. At the step SP55, the CPU 34 determines whether or not the print key 43 has been operated, to cause the printer 38 print the value of RMAX if the key 43 is operated.

If necessary, the CPU 34 causes the printer 34 also to print the specific dye disappearance curve of Cg(I) stored in the storage areas 8gl to 8gn of the RAM 35, to shift to the aforementioned biocalibration mode shown in FIG. 8B. Upon a determination that the print key 43 has not been operated at the step SP55, the CPU 34 also shifts to the biocalibration mode.

According to the embodiment of the present invention as hereinabove described, vital tissue 15 is exposed to first light signals of a wavelength absorbed by a specific dye dosed into the blood of the vital tissue, said dye to be taken in and removed by the liver, and to second light signals of a wavelength not absorbed by the specific dye. First and second photoelectric conversion signals corresponding to the first and second light signals are obtained from the vital tissue being sampled, so that the coefficient of a regression line expression between the first and second photoelectric conversion signals is determined on the basis of variable components in the blood and included in the sampled first and second photoelectric conversion signals, thereby to process a value correlated with a specific dye concentration in the blood on the basis of a sampling signal during a prescribed period after an injection of the specific dye and the determined coefficient of the regression line expression.

Thus, the index RMAX can be measured by making an ICG injection only once without taking any blood samples, whereby mental and physical burdens on the testee can be substantially reduced. Further, factors such as blood flow disturbance, vibration of the organism, pulsation in the organism, and change of the blood volume in the organism, when the sensor is attached to the tissue 15, can be prevented from adversely influencing the results to enable correct measurements.

Figure 17:
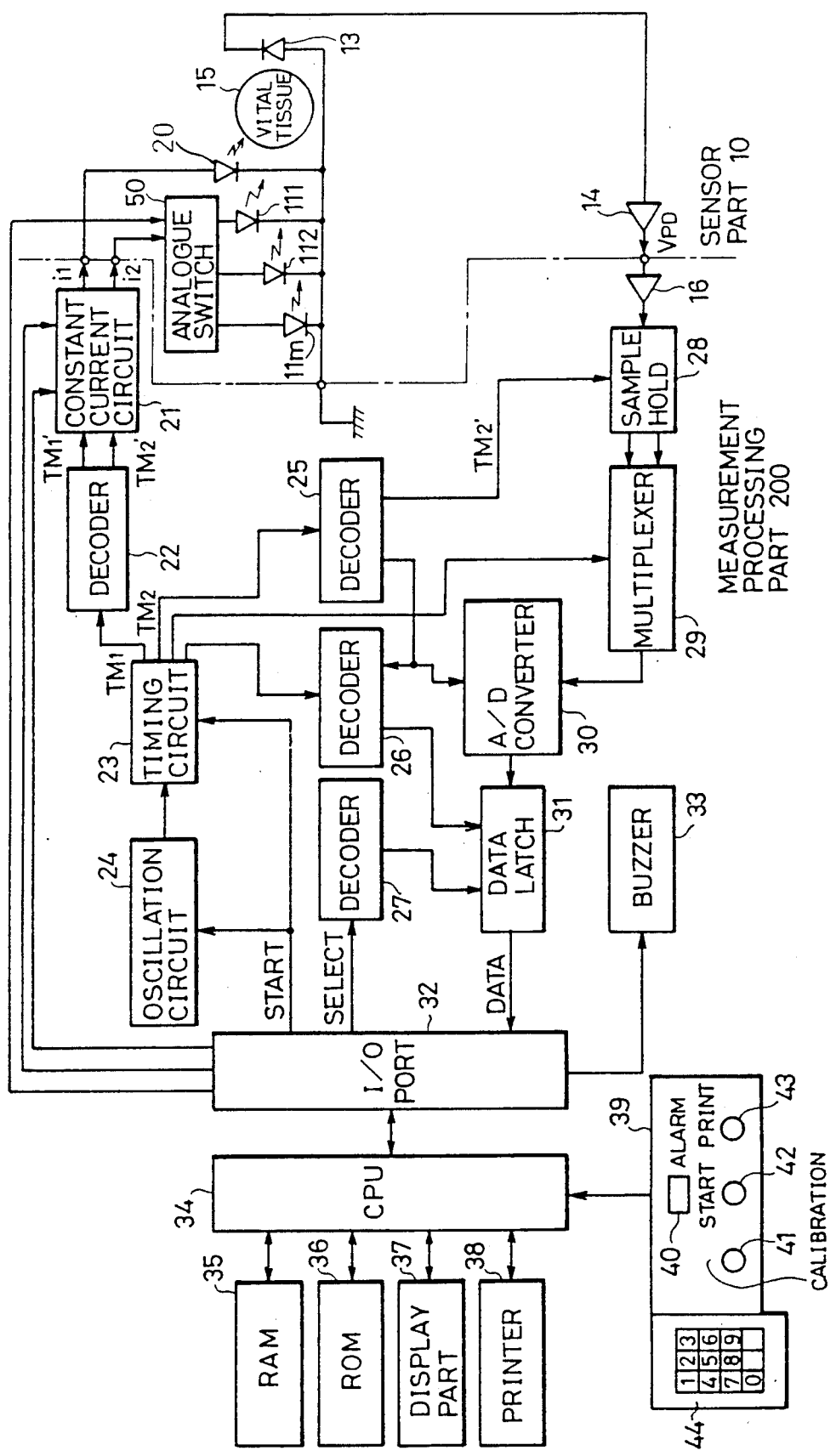
FIG. 17 is a schematic block diagram showing the structure of another embodiment of the present invention.
Figures 18, 19:
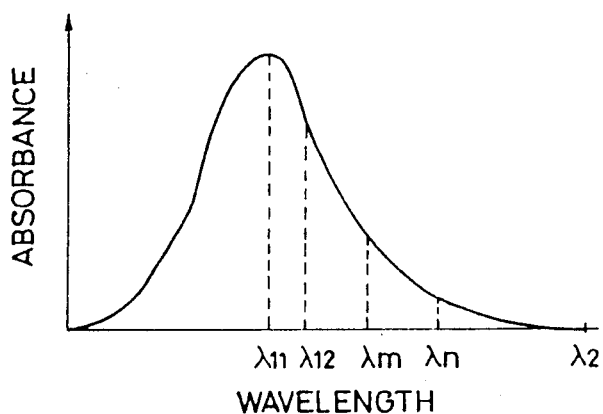
FIG. 18 illustrates the distribution of the absorbance of specific dyes.
FIG. 19 illustrates data stored in a RAM shown in FIG. 17.

FIG. 17 is a schematic block diagram showing another embodiment of the present invention, and FIG. 18 illustrates absorbance distribution of specific dyes.

The embodiment shown in FIG. 17 is structured similarly to that shown in FIG. 5, except for the following points: A function part 39 of a measurement processing part 200 is provided with an input part 44 for inputting a dose quantity D. A sensor part 10 comprises first light sources 111, 112, ..., 11m, a second light source 20, a light receiving element 13, a preamplifier 14 and an analog switch 50.

The first light sources 111, 112, ..., 11m are adapted to expose vital tissue 15 to optical pulses of wavelengths which are absorbed by specific dyes dosed into the blood of the vital tissue 15, said dye to be taken in and removed by the liver. In other words, the first light sources $11_1, 11_2, \ldots, 11_m$ respectively emit light signals of wavelengths $\lambda 1_1, \lambda 1_2, \ldots, \lambda 1_m$ having a large absorbance of the specific dyes as shown in FIG. 18, for example.

The analog switch 50 selects one of the first light sources $11_1, 11_2, \ldots, 11_m$ in response to the dose quantity inputted through the input part 45 to feed a current i1 to the same, thereby cause the selected first light source to generate a first optical pulse of a wavelength $\lambda i$. At this time, a CPU 34 controls the analog switch 50 through an I/O port 32 and si3, to select the first light source. The second light source 20 exposes the vital tissue 15 to a second optical light pulse of a wavelength $\lambda 20$ which is not absorbed by the specific dye. One of the first light sources $11_1, 11_2, \ldots, 11_m$ and the second light source 20 are driven by the measurement processing part 200 to emit light alternately in a pulse operation.

The light receiving element 13 receives the first optical pulse applied from one of the first light sources $11_1, 11_2, \ldots, 11_m$ to the vital tissue 15. As a result, the light L1 that has passed through the tissue 15 causes a respective output signal. A light pulse from the second light source 20 that has passed through the tissue 15 results in output light L2 which in turn causes a respective output signal from the element 13.

Figure 20A:
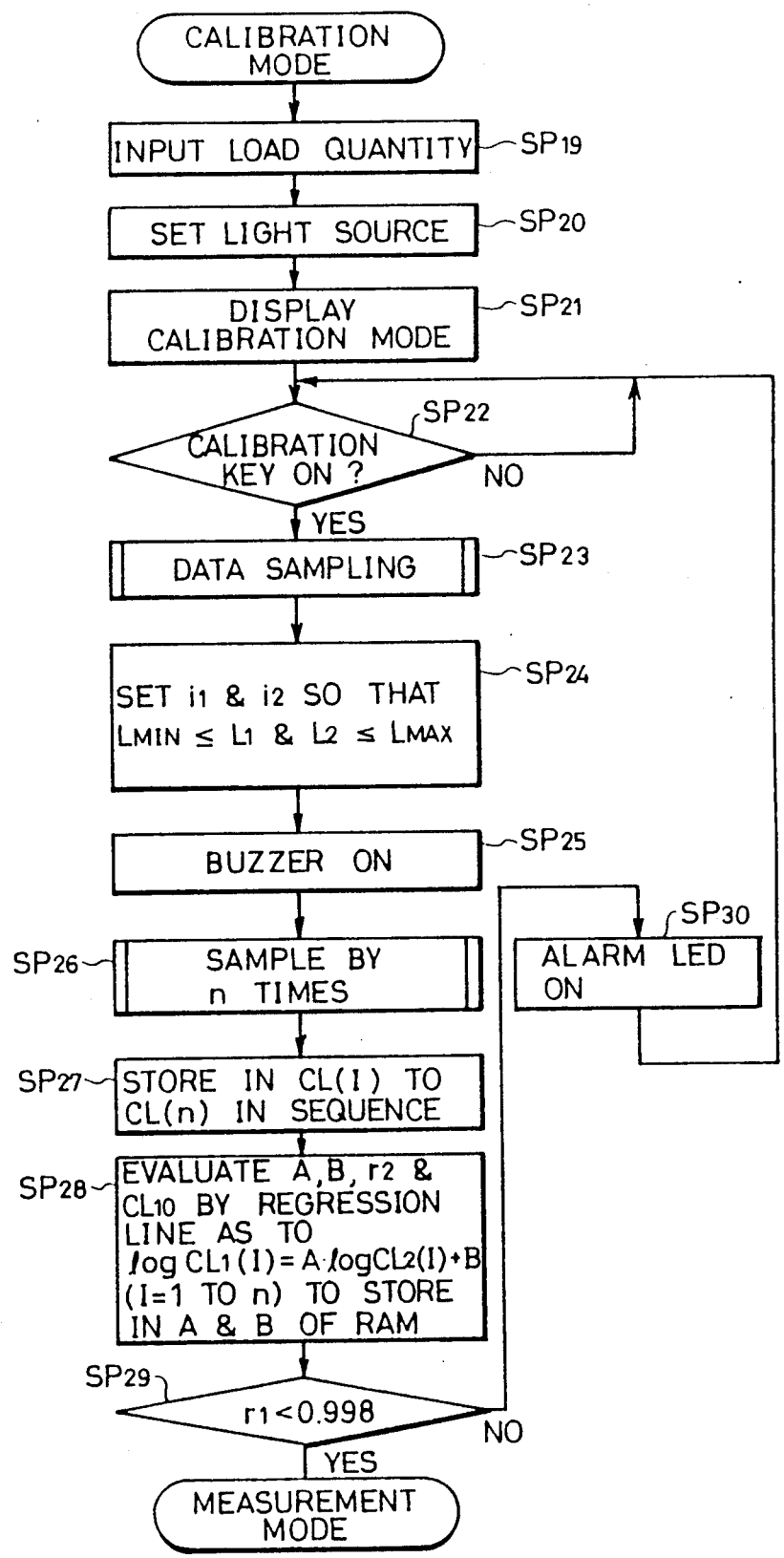
FIGS. 20A and 20B are flow charts for illustrating the operation in a calibration mode and in a measurement mode in another embodiment of the present invention.
Figure 20B:
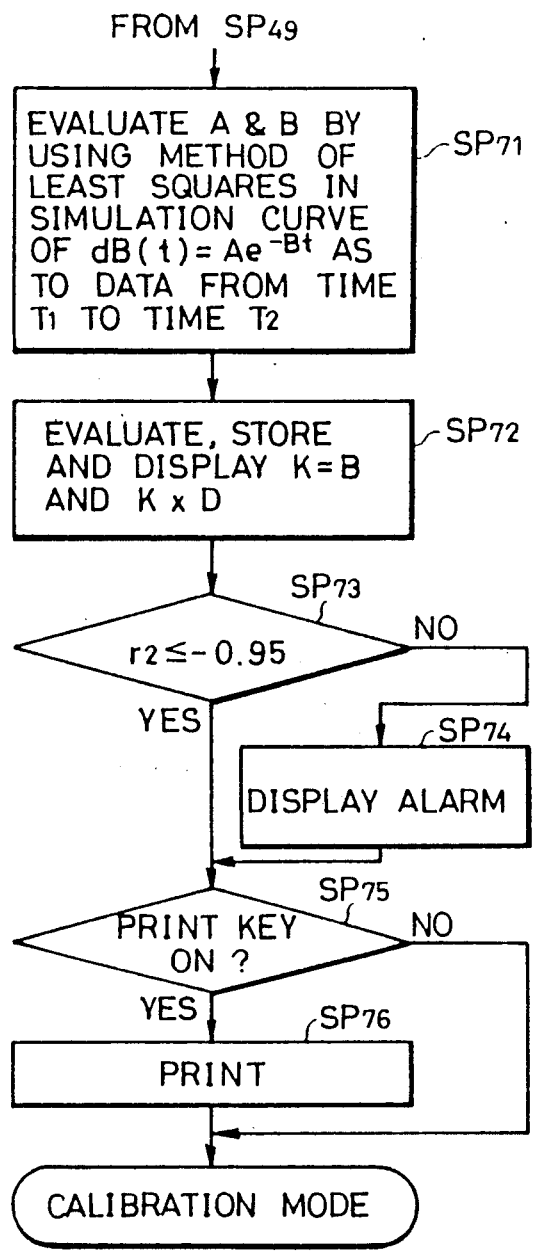
Figure 21:
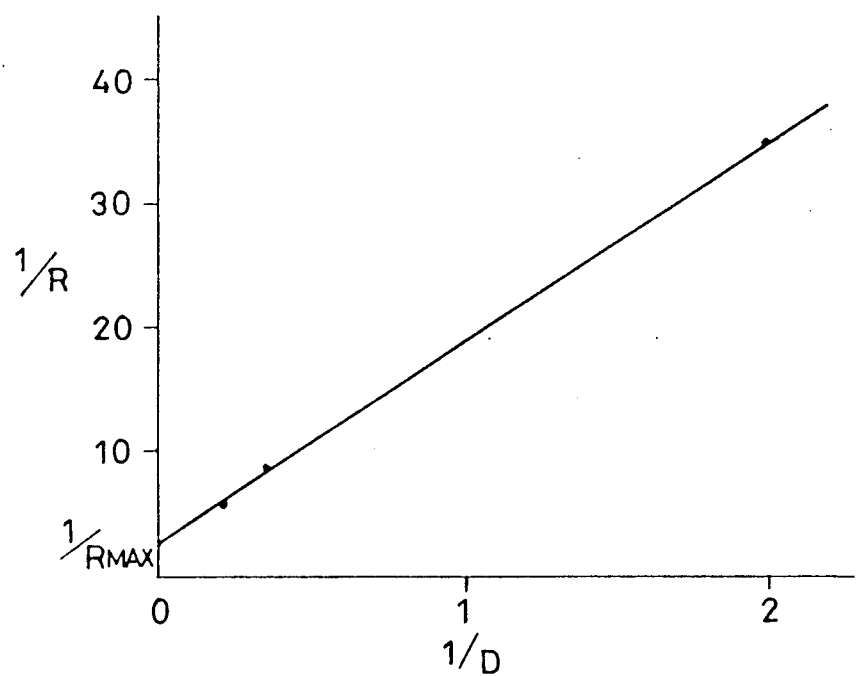
FIG. 21 is a diagram for illustrating a conventional method of measuring an index RMAX.

FIG. 19 illustrates data stored in a RAM 35 shown in FIG. 17, FIG. 20A is a flow chart for illustrating the operation of a biocalibration mode in the second embodiment of the present invention, and FIG. 20B is a flow chart for illustrating operation of a measurement mode.

The biocalibration mode shown in FIG. 20A is started when power is supplied to the apparatus or on completion of the operation of the measurement mode, similarly to the aforementioned first embodiment. At a step SP19, the CPU 34 displays in part 37 that an ICG dose quantity must be inputted. An operator recognizes this display, to input the ICG dose quantity D through the input part 44 shown in FIG. 17. This ICG dose quantity D is stored in a storage area 8j1 of the RAM 35. The CPU 34 switches the analog switch 50, in order to select a first light source corresponding to the inputted ICG dose quantity D. The CPU 34 now switches the analog switch 50 to select a first light source of a wavelength $\lambda 1_1$ when a dose quantity of 0.1 to 0.5 mg/kg is inputted, for example, while selecting a first light source of a wavelength $\lambda 1_2$ when a dose quantity of 0.5 to 1 mg/kg is inputted, for example. Operation at steps SP21 to SP30 is identical to that described above with reference to FIG. 8B.

The measurement mode is now described with reference to FIG. 20B. Upon completion of the processing at the steps SP41 to SP49 shown in FIG. 8D, the CPU 34 advances to a step SP71 shown in FIG. 20B. At the step SP71, constants A and B are obtained by simulation curves through use of the method of least squares, similarly to the aforementioned step SP51 shown in FIG. 8E. At a step SP72, the CPU 34 obtains a blood plasma disappearance rate k and a liver removal ratio R by operating $k=B$ and $R=K \cdot D$. The CPU 34 stores the obtained values k and R in storage areas 8j2 and 8j3 of the RAM 35. At this time, the CPU 34 operates a correlation coefficient r2 by the method of least squares, to process the correlation coefficient r2 stored in a storage area 8j4 of the RAM 35. Further, the CPU 34 causes a buzzer 33 to a sound completion signal at this time.

The CPU 34 displays the values k and R and the dose quantity D on the display part 37, for example. Then, the CPU 34 determines whether or not the correlation coefficient r2 is less than 0.95, for example, at a step SP73. This is to check the degree of correlation, since correlation is improved as the correlation coefficient r2 approaches $-1$. However, a value $-0.95$ is a provisional value within the range of zero to $-1$, and reliability of the numerical values is improved as the said value approaches $-1$.

If the correlation coefficient r2 is greater than 0.95, for example, the CPU 34 determines that reliability is small, to turn on an alarm LED 40 at a step SP74. If the correlation coefficient r2 is less than $-0.95$, for example, it is determined that the measurement is reliable at a step SP73, the CPU 34 advances to step SP75 without flashing an alarm at LED 40. The CPU 34 determines whether or not a print key 43 is operated at a step SP55, to cause printer 38 to print the value k, R and D if the key 43 is operated.

If necessary, the CPU 34 causes the printer 38 to print a specific dye disappearance curve of Cg(I) stored in storage areas 8g1 to 8gn of the RAM 35 and to shift to the aforementioned biocalibration mode shown in FIG. 20A. If a determination is made that the print key 43 is not operated at the step SP75, the CPU 34 also shifts to the biocalibration mode.

Figure 16:
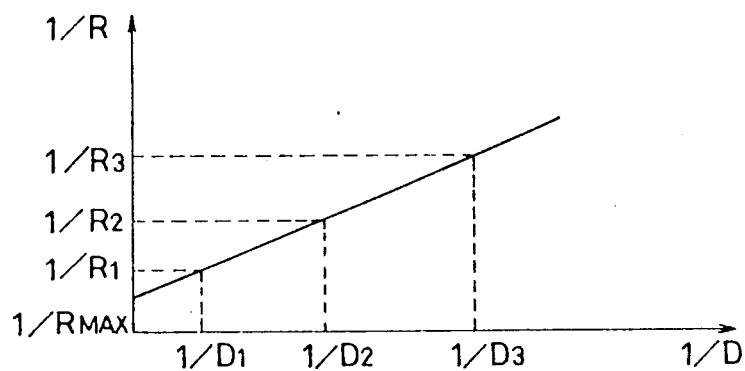

After the blood plasma disappearance rate k and the liver removal ratio R are thus obtained, ICG is again injected in a different dose quantity on the next day and the aforementioned series of operation is repeated to obtain D2 and R2. Further, ICG is newly injected on the day after next, to obtain D3 and R3. The inverse numbers 1/D of the dose quantities D and the inverse numbers 1/R of the liver removal ratios R are plotted as shown in FIG. 16 to draw a regression line, thereby to easily evaluate 1/RMAX by obtaining the intersection point of the regression line and 1/R.

According to this embodiment, as hereinabove described, a prescribed light source is automatically selected in response to the dose quantity of the specific dye, whereby a measurement can be made with the same accuracy with respect to any specific dye of any dose quantity, to effectively measure the index expressing the total amount of hepatic cell function.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A liver function testing apparatus for testing a liver function, comprising: light source means (11, 12) for exposing vital tissue (15) to a first light signal capable of being absorbed by a specific dye injected into the blood of said vital tissue, said dye to be taken in and removed by the liver, and to a second light signal capable of not being absorbed by said specific dye; photoelectric conversion means (13) for outputting first and second photoelectric conversion signals based on light from said vital tissue and corresponding to said first light signal and to said second light signal applied to said vital tissue by said light source means; sampling means (28) for sampling said photoelectric conversion outputs from said photoelectric conversion means; decision means (34, PS28) for determining a coefficient of a regression line expression between said first and second photoelectric conversion signals on the basis of variable components in said vital tissue included in said first and second photoelectric conversion signals sampled by said sampling means; arithmetic means (34, SP28) for processing a value correlated with a specific dye concentration in said blood on the basis of a sampling signal output from said sampling means during a prescribed period of time following said injection of said specific dye and said coefficient of said regression line expression determined by said decision means to obtain a coefficient of a simulation function as a function of time by using the method of least squares for processing said correlated value; and wherein said arithmetic means comprise means for obtaining an index expressing the total amount of hepatic cell function on the basis of said coefficient of said simulation function obtained by said arithmetic means.

2. The liver function testing apparatus in accordance with claim 1, wherein said light source means includes: a plurality of first light source means (111, 112, ..., 11m) for exposing said vital tissue to first light signals having different wavelengths capable of being absorbed by said specific dye, and second light source means (20) for exposing said vital tissue to a second light signal having a wavelength not absorbed by said specific dye, said liver function testing apparatus further including: input means for inputting respective dose quantities D (mg/kg) of different specific dyes, and light source selection means (50) for selecting one first light source from said plurality of first light source means in response to a dose quantity currently inputted by said input means to apply light from said one first light source to said vital tissue.

3. The liver function testing apparatus in accordance with claim 1, wherein said arithmetic means includes means (SP72) for obtaining a blood plasma disappearance rate k of said specific dye and a liver removal ration $R = D \times k$ on the basis of said coefficient of said simulation function, where k is said disappearance rate; R is indicated as mg/kg/min, and wherein D is a dye dosing value in mg/kg of dye in mg and patient weight in kg.

4. The liver function testing apparatus in accordance with claim 1, wherein said sampling means includes means for sampling said first and second photoelectric conversion signals a plurality of times, and said decision means includes means (SP28) for obtaining dimensionless constants A and B by performing a regression line analysis in accordance with the following operation expression:

$$\log CL1 = A \cdot \log C12 + B$$

wherein CL1 and CL2 represent average values of said first and second photoelectric conversion signals sampled a plurality of times by said sampling means for obtaining the maximum value of said first photoelectric conversion signal sampled a plurality of times.

5. The liver function testing apparatus in accordance with claim 1, wherein said means for obtaining said index includes means (SP51, 57–62) for injecting said specific dye, dividing a prescribed time interval following a uniform dye distribution of said specific dye in said blood, into a plurality of time blocks to obtain coefficients Ai and Bi on the basis of a simulation function $Dg = Ai \cdot e^{Bit}$ in respective blocks, wherein $i = 1, 2, \ldots, m$; $m \leq 2$, where $i = 1$ is a first time block, and t is time in minutes, and to obtain values of Cg at initial times of respective blocks as Ci whereby $Ki = -Bi$ and performing a regression line analysis on the basis of obtained coefficients Ki and Ci by an operation expression of $(1/Ki \cdot Ci) = a(1/Ci) + b$ to obtain coefficients a and b, thereby to obtain an index RMAX on the basis of an operation expression of $RMAX = 1/b$.

6. The liver function testing apparatus in accordance with claim 1, wherein said means for obtaining said index includes means for injecting said specific dye, dividing a prescribed time interval following a uniform dye distribution of said specific dye in said blood, into a plurality of time blocks to obtain coefficients Ai and Bi on the basis of a simulation function of $Cg = Ai \cdot e^{Bit}$ in respective blocks, wherein $i = 1, 2, \ldots, m$; $m \geq 2$, where $i = 1$ is a first time block and wherein t is time in minutes, and to obtain, on the basis of obtained coefficients Ai and a dose quantity D1 of said specific dye, Di by an operation expression of $Di = D1 \cdot Ci/A1$, wherein $i \geq 2$, where Di is a first time block and Ci is a value of Cg at the first time of each block, and wherein $Ki = -Bi$, and performing a regression line analysis based on an operation expression of $(1/Ki \cdot Di) = C(1/Di) + d$ on the basis of said Ki and Di to obtain coefficients C and d, thereby to obtain an index RMAX from $RMAX = 1/d$.

7. The liver function testing apparatus in accordance with claim 1, wherein
said decision means includes means (34) for processing a correlation coefficient of said regression line expression.

8. The liver function testing apparatus in accordance with claim 7, further including informing means for giving an alarm when said correlation coefficient of said regression line expression is greater than a predetermined value.

9. The liver function testing apparatus in accordance with claim 1, wherein
said arithmetic means includes means for processing a correlation coefficient of said simulation function.

10. The liver function testing apparatus in accordance with claim 1, further including informing means for giving an alarm when said correlation coefficient of said simulation function is greater than a predetermined value.

11. The liver function testing apparatus in accordance with claim 1, further including mode selection means for selecting a biocalibration mode for determining said coefficient of said regression line expression by said decision means, and a measurement mode for performing processing said specific dye correlated value by said arithmetic means.

12. The liver function testing apparatus in accordance with claim 11, further including means for activating said decision means in response to a selection of said biocalibration mode by said mode selection means.

13. The liver function testing apparatus in accordance with claim 11, further including means for activating said arithmetic means in response to a selection of said measurement mode by said mode selection means.

14. The liver function testing apparatus in accordance with claim 1, further including set means for setting intensity levels of said first light signal and said second light signal emitted from said light source means so that levels of said first and second photoelectric conversion signals are within a predetermined range.

15. The liver function testing apparatus in accordance with claim 1, further including output means for outputting said operated index RMAX.

* * * * *